(12) United States Patent
Gobber et al.

(10) Patent No.: US 11,364,315 B2
(45) Date of Patent: Jun. 21, 2022

(54) AIR FRESHENER FOR VEHICLES

(71) Applicant: ZOBELE HOLDING S.P.A., Trento (IT)

(72) Inventors: Cedric Gobber, Barcelona (ES); Jordi Guiu Pont, Barcelona (ES)

(73) Assignee: Zobele Holding S.p.A., Trento (IT)

( * ) Notice: Subject to any disclaimer, the term of this patent is extended or adjusted under 35 U.S.C. 154(b) by 0 days.

(21) Appl. No.: 15/573,844

(22) PCT Filed: May 13, 2016

(86) PCT No.: PCT/EP2016/060836
§ 371 (c)(1),
(2) Date: Nov. 14, 2017

(87) PCT Pub. No.: WO2016/180965
PCT Pub. Date: Nov. 17, 2016

(65) Prior Publication Data
US 2018/0256769 A1        Sep. 13, 2018

(30) Foreign Application Priority Data

May 14, 2015   (ES) ................................ ES201530656

(51) Int. Cl.
*A61L 9/12*         (2006.01)
*B60H 3/00*        (2006.01)

(52) U.S. Cl.
CPC .............. *A61L 9/12* (2013.01); *B60H 3/0028* (2013.01); *A61L 2209/133* (2013.01)

(58) Field of Classification Search
CPC .. A61L 9/12; A61L 2209/133; A61L 2209/15; A61L 9/122; A61L 9/125;
(Continued)

(56) References Cited

U.S. PATENT DOCUMENTS

| 2,809,863 A |   | 10/1957 | Curran ............................ 299/24 |
| 4,155,500 A | * | 5/1979 | Dutcher .................... A61L 9/12 |
|             |   |         | 229/120 |

(Continued)

FOREIGN PATENT DOCUMENTS

| DE | 696 17 399 T2 | 5/2002 |
| ES | 2 019 539 A6 | 6/1991 |

(Continued)

OTHER PUBLICATIONS

International Search Report dated Jun. 28, 2016 in corresponding PCT International Application No. PCT/EP2016/060836.
(Continued)

*Primary Examiner* — Qingzhang Zhou
*Assistant Examiner* — Juan C Barrera
(74) *Attorney, Agent, or Firm* — Ostrolenk Faber LLP

(57) ABSTRACT

An air freshener for vehicles including a casing housing a receptacle containing volatile substances and at least one fixing element, which can be fixed to an interior vent grille of a vehicle. The casing and the at least one fixing element are made of cardboard, enabling the obtainment of an air freshener at low cost compared to conventional air fresheners, since it does not require investment in moulds.

8 Claims, 4 Drawing Sheets

(58) Field of Classification Search
CPC ......... A61L 9/127; A61L 9/16; B60H 3/0028; B60H 3/0007; B60H 1/34; B60R 2011/0008; B60R 2011/0059; A01M 1/2044; A01M 1/2055; B65D 5/18; B65D 5/08; B65D 5/10; B65D 5/106; B65D 5/20–2095; B65D 5/5035; B65D 5/5059; B42D 15/042; F16B 9/023; Y10S 206/806; Y10S 229/922; Y10S 261/88; Y10S 428/905
USPC ....... 239/34–60; 206/0.5; 224/585, 424, 483
See application file for complete search history.

(56) References Cited

U.S. PATENT DOCUMENTS

| | | | | |
|---|---|---|---|---|
| 4,813,344 | A | 3/1989 | Greif | 98/2.11 |
| 5,678,763 | A * | 10/1997 | Scheuer | A61L 9/12 239/54 |
| 5,762,549 | A | 6/1998 | Scheuer et al. | 454/157 |
| 5,961,043 | A * | 10/1999 | Samuelson | A01M 1/2044 206/486 |
| 6,123,906 | A * | 9/2000 | Farmer | A61L 9/12 239/36 |
| 6,736,335 | B2 * | 5/2004 | Cuthbert | A45D 40/0087 239/326 |
| D737,947 | S * | 9/2015 | Dobler | D23/368 |
| 2014/0048545 | A1 * | 2/2014 | Kunesh | A61L 9/12 220/666 |

FOREIGN PATENT DOCUMENTS

| | | | | |
|---|---|---|---|---|
| GB | 2 251 792 A | | 7/1992 | |
| GB | 2251792 A | * | 7/1992 | ............... A61L 9/12 |
| GB | 2 263 404 A | | 7/1993 | |
| JP | H03-92701 | | 9/1991 | |
| WO | WO 2015/038284 A1 | | 3/2015 | |

OTHER PUBLICATIONS

Written Opinion dated Jun. 28, 2016 in corresponding PCT International Application No. PCT/EP2016/060836.

* cited by examiner

AIR FRESHENER FOR VEHICLES

CROSS-REFERENCE TO RELATED APPLICATIONS

The present application is a 35 U.S.C. §§ 371 national phase conversion of PCT/EP2016/060836, filed May 13, 2016, which claims priority to Spanish Patent Application No. P201530656, filed May 14, 2015. The entire contents of both applications are incorporated in full herein by reference. The PCT International Application was published in the English language.

The present invention relates to an air freshener for vehicles, in particular, a single-use air freshener at low cost compared to air fresheners for conventional vehicles.

BACKGROUND OF THE INVENTION

The use of air fresheners in the interior of vehicles is well known in the market. Interior air fresheners for vehicles comprise a plastic casing that envelopes the replacement with the volatile substances and a plastic fixing element. This fixing element helps to maintain the air freshener at a certain distance from the dashboard and in the correct position in the vehicle grille.

The major drawback of these products is that, since the parts (casing and fixing element) are made of plastic, the investments to be made in moulds are high, which implies that the product is also expensive on the market.

Therefore, the object of the present invention is to provide an air freshener for vehicles whose cost is as low as possible, without implying expensive investments in moulds.

DESCRIPTION OF THE INVENTION

The air freshener for vehicles of the invention resolves the aforementioned drawbacks and has other advantages that will be described below.

The air freshener for vehicles in accordance with the present invention comprises a casing which houses a receptacle of volatile substances and at least one fixing element that can be fixed to an interior vent grille of a vehicle and is characterised in that the casing and said at least one fixing element are made of cardboard.

Advantageously, said casing and said at least one fixing element are formed from two cardboard sheets joined together, said receptacle of volatile substances being fixed between said two cardboard sheets.

According to a preferred embodiment, the air freshener for vehicles in accordance with the present invention comprises two fixing elements, which are two tongues.

Additionally, said tongues advantageously comprise a fold line at their end nearest to the casing and each tongue preferably comprises a fixing slot.

Advantageously, the air freshener for vehicles in accordance with the present invention also comprises an external board, which is joined to the casing and to said at least one fixing element by means of a pre-die cut line, said external board being made preferably of cardboard. This external board is envisaged to be used with the air freshener's container itself and, to this end, may comprise a hole for placing it on a display stand for direct sale to the public.

Due to these characteristics, a very low-cost air freshener for vehicles is achieved which enables it to be a single-use air freshener, since it does not require the use of moulds for the manufacture thereof.

BRIEF DESCRIPTION OF THE DRAWINGS

In order to make the foregoing more readily understandable, a set of drawings is attached, wherein, schematically and by way of illustration and not limitation, a practical embodiment is represented.

DESCRIPTION OF A PREFERRED EMBODIMENT

The air freshener for vehicles in accordance with the present invention is intended for its use fixed to a vent grille of the vehicle, in the manner of conventional plastic air fresheners.

The air freshener comprises a casing 1 housing a receptacle 2 containing volatile substances, which are evaporated into the ambient air, said evaporation being facilitated by the vehicle's ventilation system.

The fixation of the casing 1 to the vent grille of the vehicle is carried out by means of at least one fixing element 3, preferably by means of two tongues, as can be observed in the figures.

In accordance with the invention and as opposed to conventional vehicle air fresheners, the casing 1 and tongues 3 are made of cardboard, such that their manufacture is much simpler and cheaper than the manufacture of air fresheners containing plastic parts requiring the manufacture of appropriate moulds.

Figure 1:
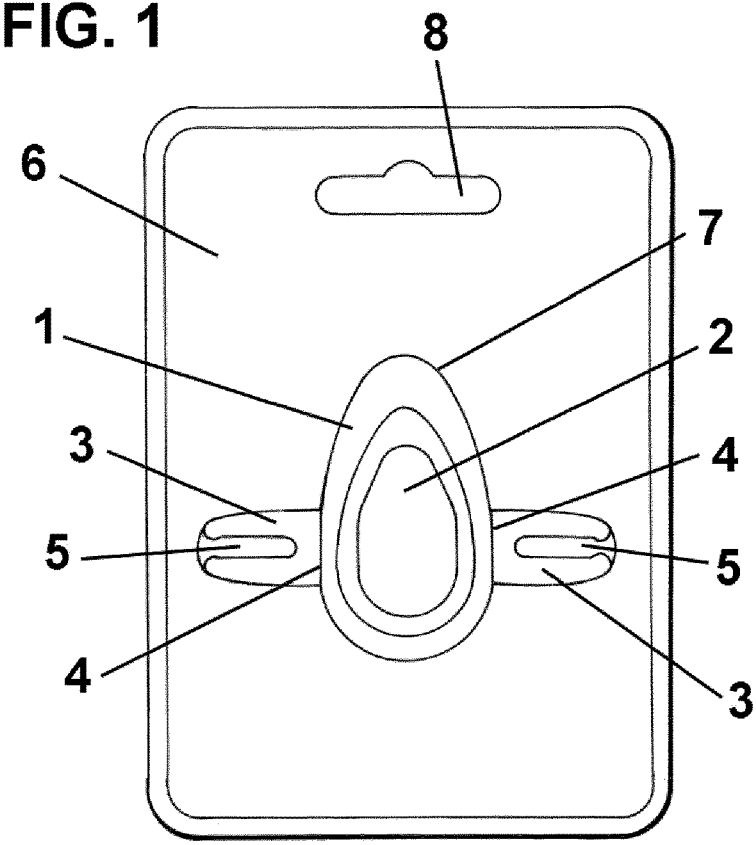
FIG. 1 shows a front view of a first embodiment of the air freshener for vehicles in accordance with the present invention.
Figure 2:
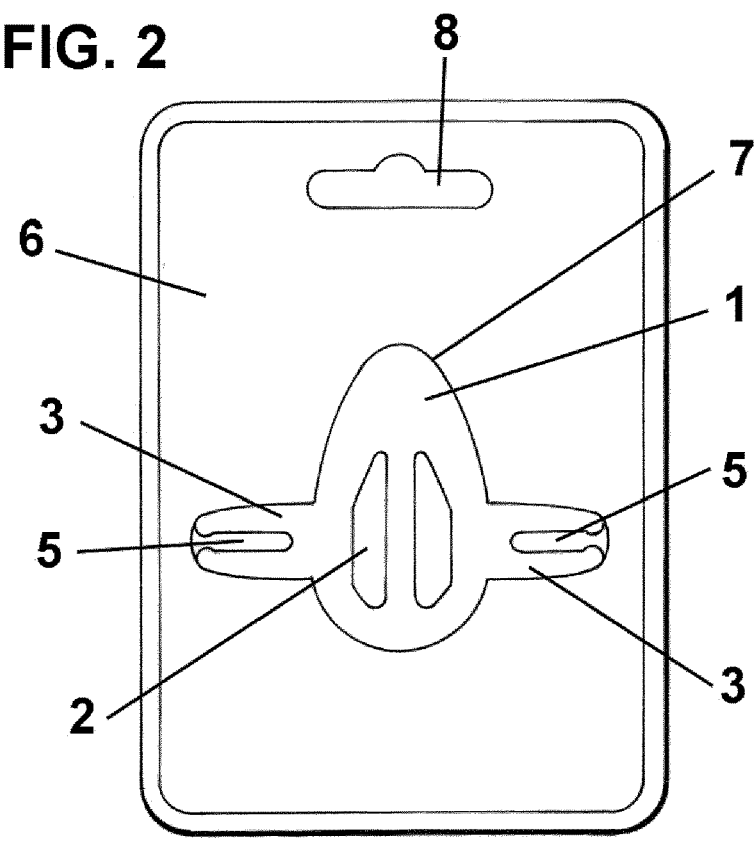
FIG. 2 shows a rear view of the first embodiment of the air freshener for vehicles in accordance with the present invention.
Figure 3:
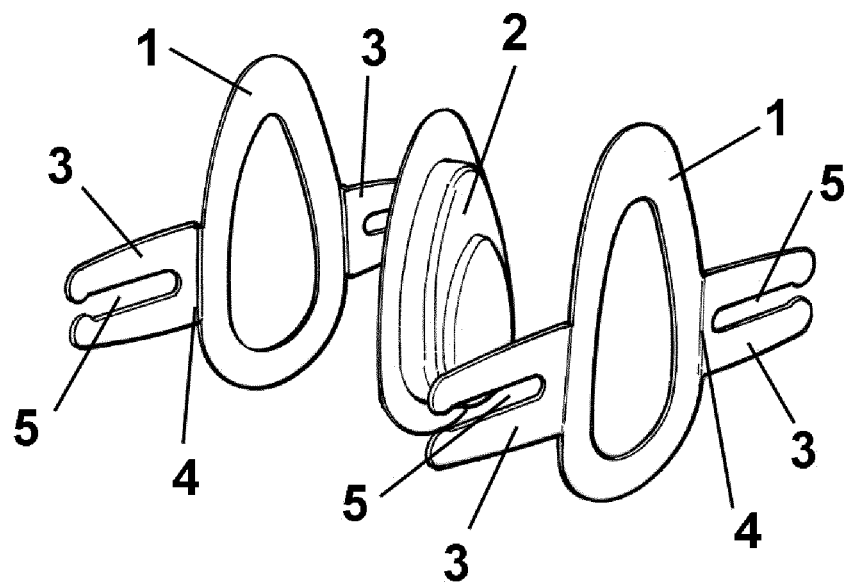
FIG. 3 shows an exploded perspective view of the first embodiment of the air freshener for vehicles in accordance with the present invention.
Figure 4:
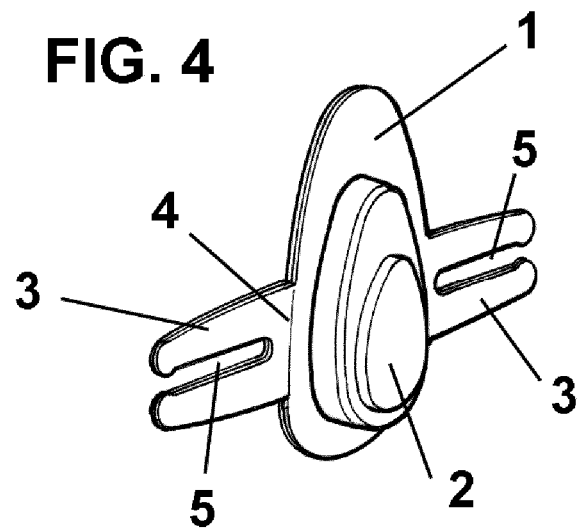
FIG. 4 shows a perspective view of the first embodiment of the air freshener for vehicles in accordance with the present invention.

In order to assemble the receptacle 2, the casing 1 and tongues 3 are formed from two cardboard sheets joined together, such that the receptacle 2 is arranged between the two sheets, preferably projecting through an opening, as can be observed in FIG. 3.

In order to facilitate its installation in the vent grille of the vehicle, the tongues 3 comprise a fold line 4 at their end nearest to the casing 1, such that in their use position the tongues 3 are approximately perpendicular to the plane defined by said casing 1.

Additionally, in order to fix it to the vent grille of the vehicle, each tongue 3 advantageously comprises a fixing slot 5, in the interior of which a slat of the vent grille is introduced when the air freshener is arranged in its use position.

The air freshener of the present invention also comprises an external board 6 that envelopes the casing 1 and the tongues 3 before the first use of the air freshener. The union between the external board 6, the casing 1 and the tongues 3 is executed by means of a pre-die cut line 7.

Therefore, the air freshener in accordance with the present invention is sold as an assembly, formed by the external board 6, which is also made of cardboard, the casing 1 and the tongues 3. In order to facilitate the storage thereof, the external board 6 comprises a hole 8 located on its upper portion so it can be hanged from a display stand inside a shop.

When the user wishes to use the air freshener, he or she simply has to separate the casing 1, receptacle 2 and tongue 3 assembly, which is facilitated by the pre-die cut line 7.

Once this assembly has been separated, the user must fold the tongues 3 such that they are substantially perpendicular to the plane defined by the casing 1, so as to allow the fixation thereof to the vent grille of a vehicle.

It should be noted that the air freshener in accordance with the present invention is not designed to be recharged, but its low cost allows it to be single-use.

Figure 5:
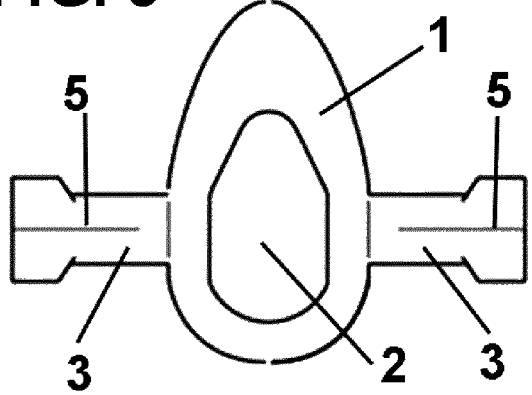
FIGS. 5 and 6 show front views of a second and third embodiments of the air freshener for vehicles in accordance with the present invention.
Figure 6:
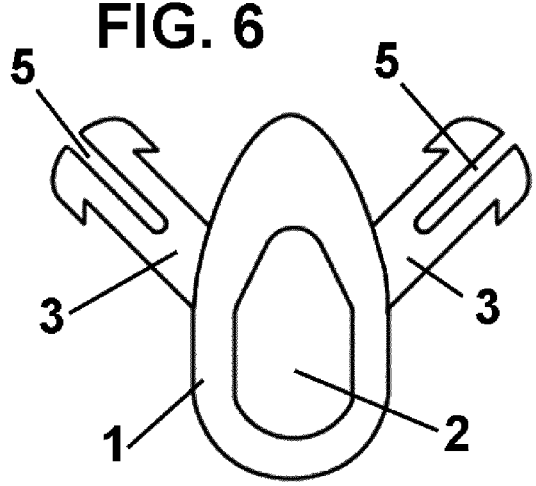
Figure 7:
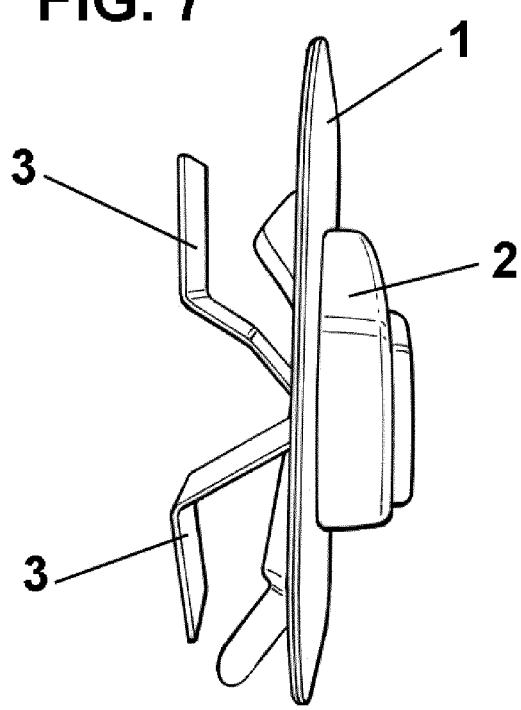
FIG. 7 shows a side view of a fourth embodiment of the air freshener for vehicles in accordance with the present invention.

FIGS. 5 to 7 represent three alternative embodiments of the air freshener represented in FIGS. 1 to 4 and described above.

For the sake of simplicity, the same numerical references are used to identify the same parts of the air freshener.

The second embodiment (represented in FIG. 5) only differs from the first embodiment in the shape of the tongues 3, which evidently may adopt any appropriate shape.

As regards to the third embodiment (represented in FIG. 6), the main difference is the arrangement of the tongues 3, which are not substantially perpendicular relative to the longitudinal axis of the casing 1, but rather are arranged forming a right or acute angle to each other, as can be observed in FIG. 5.

In the fourth embodiment (represented in FIG. 7), the main difference is that the tongues 3 comprise a transverse fold line, such that the tongues 3 remain in the position represented in this figure for their fixing to the vent grille of the vehicle.

Despite the fact that reference has been made to a specific embodiment of the invention, it is evident to the person skilled in the art that the described air freshener for vehicles is susceptible of many variations and changes, and that all the aforementioned details may be replaced with other, technically equivalent ones without detracting from the scope of protection defined by the attached claims.

The invention claimed is:

1. An air freshener for a vehicle with an interior vent grille, the air freshener comprising:
    a casing made of a first cardboard sheet and a second cardboard sheet;
    a receptacle positioned in the casing between the first and second cardboard sheets, the receptacle configured to contain volatile substances; and
    the first cardboard sheet comprising at least one fixing element made of cardboard on a first side of the receptacle and at least one second fixing element positioned on a second side of the receptacle;
    the second cardboard sheet comprising at least one third fixing element on the first side of the receptacle and at least one fourth fixing element on the second side of the receptacle, the first and third fixing elements forming a first tongue and the second and fourth fixing elements forming a second tongue,
    wherein said receptacle containing volatile substances is retained between said first and second cardboard sheets,
    wherein in a use position the first and second tongues are fixed to the interior vent grille and the first and second tongues extend away from the casing such that their longitudinal extents are transverse to a longitudinal extent of the casing.

2. The air freshener for vehicles according to claim 1, wherein said tongues comprise a fold line at their end nearest to the casing.

3. The air freshener for vehicles according to claim 1, wherein each tongue comprises a pair of projections separated by a fixing slot such that each tongue is configured to be fixed to the interior vent grille by the pair of projections securing a part of the interior vent grille positioned between the pair of projections.

4. The air freshener for vehicles according to claim 1, further comprising an external board that is joined to the casing and to said at least one fixing element by a pre-die cut line.

5. The air freshener for vehicles according to claim 4, wherein said external board is made of cardboard.

6. The air freshener for vehicles according to claim 1, wherein a major side of the casing lies along a primary plane, and in the use position the longitudinal extents of the first and second tongues are transverse to the primary plane.

7. The air freshener for vehicles according to claim 1, wherein the receptacle comprises a projecting portion and peripheral lip around the projecting portion,
    the first cardboard sheet comprises an aperture positioned to receive the projecting portion of the receptacle and to obstruct the peripheral lip of the receptacle,
    the first and second cardboard sheets in the use position retain the receptacle by the projecting portion of the receptacle projecting through the aperture of the first cardboard sheet, and the first and second cardboard sheets securing therebetween the peripheral lip.

8. An air freshener for a vehicle comprising an interior vent grille, the air freshener comprising:
    a casing made of a first cardboard sheet and a second cardboard sheet;
    a receptacle positioned in the casing between the first and second cardboard sheets and retained thereby, the receptacle configured to contain volatile substances; and
    the first cardboard sheet comprising at least one fixing element made of cardboard on a first side of the receptacle and at least one second fixing element positioned on a second side of the receptacle;
    the second cardboard sheet comprising at least one third fixing element on the first side of the receptacle and at least one fourth fixing element on the second side of the receptacle;
    the first and third fixing elements forming a first tongue and the second and fourth fixing elements forming a second tongue, each tongue comprising a pair of projections separated by a fixing slot such that each tongue is configured to be fixed to the interior vent grille by the pair of projections securing a part of the interior vent grille positioned between the pair of projections.

* * * * *